US008784408B2

(12) United States Patent
DeLand et al.

(10) Patent No.: US 8,784,408 B2
(45) Date of Patent: *Jul. 22, 2014

(54) LED TREATMENT OF DERMATOLOGIC TOXICITIES ASSOCIATED WITH VASCULAR ENDOTHELIAL GROWTH FACTOR INHIBITORS

(76) Inventors: M. Maitland DeLand, Lafayette, LA (US); Robert A. Weiss, Baltimore, MD (US)

(*) Notice: Subject to any disclaimer, the term of this patent is extended or adjusted under 35 U.S.C. 154(b) by 128 days.

This patent is subject to a terminal disclaimer.

(21) Appl. No.: 13/020,313

(22) Filed: Feb. 3, 2011

(65) Prior Publication Data

US 2011/0196352 A1    Aug. 11, 2011

Related U.S. Application Data

(60) Provisional application No. 61/301,857, filed on Feb. 5, 2010.

(51) Int. Cl.
*A61B 18/18*    (2006.01)

(52) U.S. Cl.
USPC .................................. 606/9; 607/88

(58) Field of Classification Search
CPC ............... A61B 18/203; A61B 2018/00476; A51B 2018/00452; A61N 5/062; A61N 2005/0652; A61N 5/0601
USPC .................................. 606/9; 607/88
See application file for complete search history.

(56) References Cited

U.S. PATENT DOCUMENTS

| | | | |
|---|---|---|---|
| 6,060,083 A | 5/2000 | Dorr et al. | |
| 6,629,971 B2 | 10/2003 | McDaniel | |
| 6,676,655 B2 | 1/2004 | McDaniel | |
| 6,887,260 B1 | 5/2005 | McDaniel | |
| 6,936,044 B2 | 8/2005 | McDaniel | |
| 7,004,933 B2 | 2/2006 | McDaniel | |
| 7,044,933 B2 | 5/2006 | VanDiver et al. | |
| 7,107,997 B1 | 9/2006 | Moses et al. | |
| 7,201,765 B2 | 4/2007 | McDaniel | |
| 7,494,503 B2 | 2/2009 | McDaniel | |
| 7,507,228 B2 | 3/2009 | Sun et al. | |
| 2002/0123746 A1 | 9/2002 | McDaniel | |
| 2003/0004499 A1 | 1/2003 | McDaniel | |
| 2003/0129154 A1 | 7/2003 | McDaniel | |
| 2003/0144236 A1 | 7/2003 | Weiss | |
| 2004/0267236 A1 | 12/2004 | Sun et al. | |
| 2005/0053938 A1* | 3/2005 | Kohler | 435/6 |
| 2005/0149150 A1 | 7/2005 | McDaniel | |
| 2005/0261750 A1 | 11/2005 | McDaniel | |
| 2005/0283211 A1 | 12/2005 | McDaniel | |
| 2006/0129209 A1 | 6/2006 | McDaniel | |
| 2006/0184214 A1 | 8/2006 | McDaniel | |
| 2006/0212025 A1 | 9/2006 | McDaniel | |
| 2006/0217690 A1 | 9/2006 | Bastin et al. | |
| 2006/0265030 A1 | 11/2006 | McDaniel | |
| 2006/0280660 A1 | 12/2006 | Weiss | |
| 2007/0191822 A1 | 8/2007 | McDaniel | |
| 2008/0097278 A1 | 4/2008 | Cole et al. | |
| 2009/0131499 A1 | 5/2009 | Castro et al. | |
| 2009/0196903 A1 | 8/2009 | Kliman | |
| 2009/0311347 A1 | 12/2009 | Oronsky et al. | |
| 2010/0256550 A1 | 10/2010 | McDaniel | |
| 2011/0196351 A1* | 8/2011 | DeLand et al. | 606/9 |
| 2011/0196353 A1* | 8/2011 | DeLand et al. | 606/9 |

OTHER PUBLICATIONS

Mayo Clinic website, Jun. 9, 2009 [online] [retrieved on May 22, 2013] Retrieved from Mayo Clinic website using internet and wayback machine: http://web.archive.org/web/20090609165452/http://www.mayoclinic.com/health/sebaceous-cysts/DS00979/DSECTION=causes.*
International Search Report dated May 11, 2011 in related PCT Application No. PCT/US11/23567 filed Feb. 3, 2011, 2 pages.
International Search Report dated Apr. 20, 2011 in related PCT Application No. PCT/US11/23572 filed Feb. 3, 2011, 2 pages.
International Search Report dated May 10, 2011 in related PCT Application No. PCT/US11/23575 filed Feb. 3, 2011, 2 pages.
Lacouture et al., Evolving Strategies for the Management of Hand-Foot Skin Reaction Associated with the Multitargeted Kinase Inhibitors Sorafenib and Sunitinib, The Oncologist, 2008, pp. 1001-1011, vol. 13.
Perez-Soler et al., HER1/EFGR Inhibitor-Associated Rash: Future Directions for Management and Investigation Outcomes from the HER1/EGFR Inhibitor Rash Management Forum, The Oncologist, 2005, pp. 345-356, vol. 10.
DeLand et al., Treatment of Radiation-Induced Dermatitis With Light-Emitting Diode (LED) Photomodulation, Lasers Surg Med, 2007, pp. 164-168, vol. 39.
Huang et al., In vitro observations on the influence of copper peptide aids for the LED photoirradiation of fibroblast collagen synthesis, Photomedicine and Laser Surgery, 2007, vol. 25, No. 3.
Lacouture, Mechanisms of cutaneous toxicities to EGFR inhibitors, Nature Reviews, 2006, vol. 6.

(Continued)

*Primary Examiner* — Gary Jackson
*Assistant Examiner* — Sebastian X Lukjan
(74) *Attorney, Agent, or Firm* — Eric Sophir; Dentons US LLP

(57) ABSTRACT

The present invention relates generally to methods of preventing or treating toxicities of the skin, hair, and/or nails, which are associated with administration of one or more vascular endothelial growth factor receptor inhibitors, with light-emitting diode photomodulation treatment, either alone or in combination with other agents.

22 Claims, No Drawings

(56) References Cited

OTHER PUBLICATIONS

McDaniel et al., Varying ratios of wavelengths in dual wavelength LED photomodulation alters gene expression profiles in human skin fibroblasts, Lasers in Surgery and Medicine, 2010, pp. 540-545, vol. 42.

Weiss, Comparison of non ablative fibroblast photoactivation with and without application of topical cosmeutical agents, Lasers Surg Med, 2003, vol. 15, No. 23.

Weiss et al., Clinical Trial of a Novel Non-Thermal LED Array for Reversal of Photoaging: Clinical, Histologic, and Surface Profilometric Results, Lasers Surg Med, vol. 36, pp. 85-91, 2005.

Weiss, LED Low Level Light Therapy, Facial Rejuvenation, 2007, pp. 71-78.

* cited by examiner

LED TREATMENT OF DERMATOLOGIC TOXICITIES ASSOCIATED WITH VASCULAR ENDOTHELIAL GROWTH FACTOR INHIBITORS

This application claims the benefit of priority to U.S. Provisional Application No. 61/301,857, filed on Feb. 5, 2010, the contents of which are hereby incorporated by reference in their entirety.

FIELD OF INVENTION

The present invention relates generally to methods of preventing or treating toxicities of the skin, hair, and/or nails, which are associated with administration of one or more vascular endothelial growth factor inhibitors, using light-emitting diode photomodulation treatment, either alone or in combination with other agents.

BACKGROUND OF THE INVENTION

Vascular endothelial growth factor (VEGF) is a proangiogenic factor that is secreted by tumor cells to stimulate endothelial cells to proliferate and form new blood vessels. Angiogenesis, which is the process by which new blood vessels are formed from the existing vasculature, is essential for the development and continuing growth of human tumors, and is necessary for the formation of metastases. Inhibiting angiogenesis is an important goal in the treatment of a variety of cancers, and therefore VEGF has become an important drug target for the prevention and treatment of these cancers. Drugs developed to inhibit VEGF target either VEGF itself, or one of the VEGF receptors.

Among the commonly used VEGF inhibitors in cancer therapy are bevacizumab (Avastin®), ranibizumab (Lucentis®), sunitinib (Sutent®), sorafenib (Nexavar®), axitinib, and pazopanib.

A side of effect of treatment with VEGF inhibitors is the presentation of dermatologic toxicities that can manifest on many areas of the body, and in particular, the hands and feet, as well as on the face, cheeks, and back of patients; toxicities also present on the nails and affect hair follicles are hair growth. The dermatologic toxicities can include hand-foot syndrome, acneiform rashes such as papulopustular rashes, as well as psoriasis, pruritus, paronychia, and changes in hair growth. Patients may also develop various other skin rashes, and problems relating to the eyelids and eyelashes. Hand and foot blisters are often associated with VEGF inhibitor treatment. Because hand and foot surfaces are under pressure from walking and other activity, the skin in these areas is more sensitive, and pressure points can develop to contribute to the blisters and erythema.

These dermatologic toxicities can begin to manifest soon after VEGF inhibitor treatment or up to several months following the end of treatment. In some circumstances, conditions such as psoriasis can develop after the papulopustular rash has resolved.

The severity of the toxicities can vary throughout treatment, and can depend on the specific VEGF inhibitor used, and can even resolve, temporarily, throughout the duration of treatment. Once treatment discontinues, however, these toxicities can disappear.

Patients often discontinue VEGF inhibitor treatment as a result of the side effects. Frequently, therefore, physicians lower the VEGF inhibitor dosage to decrease the scale of the side effects, and in many cases, treatment is delayed as a result.

Importantly, there is a positive correlation between the severity of the dermatologic toxicities and how effective an VEGF inhibitor is in treating a patient's cancer. Studies demonstrate this positive correlation between development of the rash or other skin eruption, and clinical outcomes, including the extent to which a patient's tumor shrinks Therefore, a means of preventing and/or treating side effects that might hinder the administration of VEGF inhibitors is crucial.

Many treatments to manage VEGF inhibitor side effects on the skin and related areas have been attempted, including the use of tetracycline, mild cleansers, hydrocortisone, clindamycin gel, and tacrolimus cream, as well as sunscreen and analgesics. These agents have proved largely unsuccessful in treating the toxic side effects of VEGF inhibitor treatment, and therefore there is a need for additional therapies that are efficacious in preventing and treating these unpleasant side effects.

SUMMARY OF INVENTION

This invention encompasses methods of treating and preventing toxicity of the skin, hair, and nails, that is associated with the administration of VEGF inhibitors, comprising light-emitting diode (LED) photomodulation therapy, either alone or in combination with other therapies. Subjects for use with this invention are mammalian, and preferably are human. By treating patients in need of treatment using the methods of this invention one can manage, attenuate, ameliorate, or prevent the progression of skin, hair, and/or nail toxicity associated with the administration of VEGF inhibitors.

LED photomodulation therapy is particularly effective for preventing and treating toxicities associated with VEGF inhibitor administration in patients with different types of cancers, or in patients receiving VEGF inhibitors for other indications, as well as for preventing and treating symptoms of those toxicities, and infections associated with the toxicities. It has been determined that patients are accepting of LED photomodulation treatment, as the treatment is administered painlessly, easily, and generally the process is not overly time-consuming. Very little additional time is required for the patient beyond other therapies, and in many cases the LED photomodulation treatment lasts for less than 10 minutes, and often for less than 1 minute. LED photomodulation treatment therefore increases patient compliance with VEGF inhibitor therapy and thereby increases the success of treatment with VEGF inhibitor agents for different types of cancer.

In some embodiments, the method of the invention is effective for treating, preventing, and preventing the progression of toxicity to the skin, hair, and nails, that is associated with the administration of VEGF inhibitors. Skin refers to all layers of the skin, including the epidermis, the dermis, and subcutaneous layer (also known as the hypodermis or subcutis), and includes any structure or portion found within any of these layers, and any structure or portion that may traverse any of these layers, and includes, but is not limited to hair follicles and sebaceous glands.

The method of the invention comprises using LED photomodulation treatment in order to treat a subject in need thereof, either alone or in combination with other agents, to prevent or treat toxicities to the skin, hair, and/or nails that are associated with VEGF inhibitor treatment. The method comprises directing light onto a target area on said subject, the light being emitted from one or more LED sources that produces at least one range of wavelengths of light.

In one embodiment, a method is provided for preventing or treating inflammation of the skin, hair, and/or nails, associated with administration of one or more VEGF inhibitors in a subject in need thereof In one embodiment the LED source used in the method of the invention emits light at a wavelength from about 300 nm to about 1600 nm. In a preferred embodiment, the LED source emits light at a wavelength from about 550 nm to about 650 nm. In another preferred embodiment, the wavelength is about 590 nm.

In another preferred embodiment, a combination of wavelengths is used, the combination comprising about 90% of a wavelength of about 590 nm, and about 10% of a wavelength of about 870 nm.

In some embodiments, the LED source used in the method of the invention emits light in pulses. Pulses may be at various durations and intervals. In one preferred embodiment, pulses are 250 ms in duration and are repeated 100 times, and are separated by 100 ms in a single treatment.

In one preferred embodiment, the fluence for a single treatment is less than about 1.0 J/cm$^2$. In another one preferred embodiment, the fluence for a single treatment is from about 0.1 to about 0.9 J/cm$^2$. In yet another preferred embodiment, the fluence is about 0.15 J/cm$^2$. In yet another preferred embodiment, the fluence is about 0.10 J/cm$^2$.

In one embodiment, the LED phototherapy treatment according to the method of the invention is administered once daily. In some embodiments, the LED phototherapy treatment is administered beginning prior to the administration of VEGF inhibitor therapy and continues during VEGF inhibitor therapy. In other embodiments, the LED phototherapy treatment is administered concurrent with the administration of VEGF inhibitor therapy.

In one embodiment, the LED photomodulation treatment according to the method of the invention is administered following the initial dose of VEGF inhibitor therapy. In another embodiment the LED photomodulation treatment according to the method of the invention is administered starting after the final dose of VEGF inhibitor is given to a subject.

In one embodiment, a method is provided for reducing vascular dilatation in the skin, that is associated with the administration of VEGF inhibitors.

In another embodiment, a method is provided for reducing permeability and reducing activation of nociceptive fibers in skin that is associated with the administration of VEGF inhibitors.

In one embodiment, a method is provided for preventing or treating toxicity to the skin, including without limitation, the epidermal, dermal, and/or subcutaneous layer of the skin that is associated with the administration of one or more VEGF inhibitors in a subject in need thereof. The method comprises using light LED phototherapy treatment which comprises directing light onto a target area of the skin of said subject, the light being emitted from one or more LED sources that produces at least one range of wavelengths of light.

In one preferred embodiment, the method of the invention prevents or treats skin toxicity in the form of palmar-plantar erythrodysesthesia, (also referred to as "hand-foot syndrome"), or at least some of the symptoms of hand-foot syndrome, such as erythematous swellings.

In one preferred embodiment, the method of the invention prevents or treats skin toxicity in the form of an acneiform rash that is not caused by bacteria.

In another embodiment, the method of the invention prevents or treats skin toxicity in the form of a papulopustular rash. In another embodiment, the method of the invention prevents or treats skin toxicity in the form of a maculopapular rash.

In another embodiment, the method of the invention prevents or treats skin toxicity in the form pruritis.

In yet other embodiments, the method of the invention treats skin that is classified as an NCI-CTC grade 1, grade 2, grade 3, or grade 4 rash. In one preferred embodiment, the method of the invention treats skin that is classified as an NCI-CTC grade 2 or higher.

In some embodiments, the method of the invention comprises using LED photomodulation treatment and further comprises the administration of one or more additional agents. In some embodiments, the additional agent is lotion containing copper.

In one embodiment, the skin toxicity to be treated is in an area of the skin selected from the group consisting of the epidermis, the dermis, and the subcutaneous layer of the skin.

In some embodiments, LED photomodulation therapy is directed to one or more target areas, which comprise, but are not limited to the face, neck, chest, forehead, back, scalp, hands, and feet.

In a preferred embodiment, LED photomodulation therapy is directed to the face. In another preferred embodiment, LED photomodulation therapy is directed to the hands and/or feet.

In one embodiment, the VEGF inhibitor is selected from the group consisting of bevacizumab, ranibizumab, sunitinib, sorafenib, axitinib, pazopanib, vatalanib, and telatinib, semaxanib.

DETAILED DESCRIPTION

Vascular endothelial growth factor (VEGF) plays a critical role in many cancers, due to its role in angiogenesis, and therefore tumor growth and formation of metastases. VEGF plays a role in many human cancers, including, among others, breast, lung, colorectal, thyroid, prostate, head and neck, ovarian, stomach, kidney, brain, and pancreatic, as well as gioblastoma, and renal cell carcinoma, among others. Therefore, drugs targeting the VEGF system play an important role in the treatment of many different types of cancer.

This invention encompasses methods of treating and preventing toxicity of the skin, hair, and nails, that is associated with the administration of VEGF inhibitors, comprising using light-emitting diode (LED) photomodulation therapy, which is a non-thermal light therapy, either alone or in combination with other therapies. Skin refers to all layers of the skin, including the epidermis, the dermis, and subcutaneous layer (also known as the hypodermis or subcutis), and includes any structure or portion found within any of these layers, and any structure or portion that may traverse any of these layers, and includes, but is not limited to hair follicles and sebaceous glands. Subjects to be treated with this invention are mammalian, and preferably are human. By treating patients in need of treatment using the methods of this invention, one can eliminate, manage, attenuate, ameliorate, or prevent the progression of skin, hair, and nail toxicity in a subject associated with the administration of one or more VEGF inhibitors.

The method of the invention encompasses LED photomodulation treatment for preventing or treating any kind of toxicity to tissues of the body associated with the administration of VEGF inhibitors, and in particular, any area of the skin. The method of the invention also encompasses preventing or treating toxicities to the hair and nails that are associated with administration of one or more VEGF inhibitors.

The method of preventing and treating the multiple forms of skin, hair, and nail toxicities associated with VEGF inhibitor treatment is accomplished according to the invention by treating a subject in need of treatment with LED photomodulation at the affected area in need of treatment. In the method according to the invention, light from at least one LED source is directed to one or more targeted areas of a subject's skin, hair, and/or nails, for a specified duration, at a specified wavelength or range of wavelengths, in an either pulsed or continuous fashion. Treatment may begin prior to, during, or following initiation of VEGF inhibitor treatment, and can last for various amounts of time.

Any source or sources of LED known to one of ordinary skill in the art may be utilized in the methods of the invention. It is preferred that the panel which emits the light allows for uniform administration of light therapy. The LEDs may be assembled into small lamps, for example, up to about 3 mm to about 5 mm in diameter, but about 10 mm and larger lamps may also be used. LEDs may also be assembled into larger arrays or panels, which allow for higher energy intensities. Large LED panel arrays can also allow larger areas to be treated at one time, such as the entire face. For example, the LEDs may be assembled into lamps of between about 70 mm to about 100 mm inches mm in diameter. In a preferred embodiment, the LEDs are about 80 mm in diameter. The LED arrays may be arranged in such a way to reach the desired target areas on the subject, such that, for example, the contours on the face do not prevent any areas from being reached by the light.

Any source of low level light may be used, such that it emits, preferably, less than 1 J/cm$^2$. In one preferred embodiment, the device used for emitting light is Gentlewaves® (LightBioScience, LLC, Virginia Beach, Va.).

An LED or an array of LEDs can be used to emit light at one or more wavelengths, either simultaneously or consecutively, to deliver energy fluence to the targeted area or areas on the subject. The targeted cells are provided with a clinically effective fluence of energy to initiate photomodulation and/or photoregeneration, but do not receive an amount of light that could cause damage to the cells that are targeted.

In some embodiments, the array of LEDs can be used to deliver a continuous wave of light to the targeted area. Alternatively, and in a preferred embodiment, the light source may be "pulsed" according to a pattern determined to be effective depending on the nature of the targeted area and the actual or anticipated severity of symptoms. The pattern, for example, may be referred to by the duration of each pulse, the time between each pulse, and the number of pulses administered. A pattern of "250/100/100," for example, would refer to pulses of 250 milliseconds in duration, separated by 100 milliseconds, and repeated 100 times. Such a pattern may deliver the same energy fluence as a 25 second continuous wave treatment.

In one preferred embodiment, the pulse pattern is 250/100/100.

The LED array may include LED emitters that emit multiple wavelengths, a single wavelength, or the array may include multiple types of emitters, if more than one wavelength is used for treatment. Each LED will generally emit at a dominant emissive wavelength from about 300 nm to about 1600 nm. The array may include combinations of LEDs that emit in the visible and/or infrared portion of the spectrum.

Wavelength is chosen based on the particular target area to be treated and on the severity of the symptoms or anticipated symptoms to be treated or prevented, as well as on the desired effect. The wavelength or wavelengths must reach the cells of the target area to be effective, and the tissue penetration depth required may differ depending on, for example, the nature of the target area and the particular condition to be prevented or treated. For example, in most cases, the wavelength used for damaged skin is likely to be different from the wavelength used for non-damaged skin.

In one embodiment, the LED emits a single wavelength from about 300 nm to about 1600 nm. In one embodiment, the LED emits a single wavelength from about 300 nm to about 400 nm. In one embodiment, the LED emits a single wavelength from about 400 nm to about 500 nm. In one embodiment, the LED emits a single wavelength from about 500 nm to about 600 nm. In one embodiment, the LED emits a single wavelength from about 600 nm to about 700 nm. In one embodiment, the LED emits a single wavelength from about 700 nm to about 800 nm. In one embodiment, the LED emits a single wavelength from about 800 nm to about 900 nm. In one embodiment, the LED emits a single wavelength from about 900 nm to about 1000 nm. In one embodiment, the LED emits a single wavelength from about 1000 nm to about 1100 nm. In one embodiment, the LED emits a single wavelength from about 1100 nm to about 1200 nm. In one embodiment, the LED emits a single wavelength from about 1200 nm to about 1300 nm. In one embodiment, the LED emits a single wavelength from about 1300 nm to about 1400 nm. In one embodiment, the LED emits a single wavelength from about 1400 nm to about 1500 nm. In one embodiment, the LED emits a single wavelength from about 1500 nm to about 1600 nm.

In one preferred embodiment, the LED emits a single wavelength from about 400 nm to about 800 nm. In another preferred embodiment, the LED emits a single wavelength from about 500 nm to about 700 nm.

In yet another preferred embodiment, the LED emits a single wavelength from about 500 nm to about 650 nm.

In yet another preferred embodiment, the LED emits a single wavelength of about 590 nm.

In some preferred embodiments, combinations of light in the visible spectrum and light in the infrared range are emitted by the LED source or sources. In one preferred embodiment, a combination is used of visible wavelength such as yellow, from about 570 nm to about 610 nm, and infrared wavelength, from about 900 nm to about 1000 nm.

In another preferred embodiment, the combination of light comprises about 90% of a wavelength of about 590 nm, and about 10% of a wavelength of about 870 nm.

Pulse duration is determined based on the particular target area to be treated, and on the severity of the symptoms or anticipated symptoms to be treated or prevented, as well as on the desired effect. Pulse duration refers to the time over which the target area is exposed to the LED during each pulse, and in some embodiments is from about 0.1 microseconds to about 1 hour. In one embodiment, the pulse duration is from about 1.0 millisecond to about 1 hour. In another embodiment, the pulse duration is from about 10 milliseconds to about 1 hour. In another embodiment, the pulse duration is from about 20 milliseconds to about 1 hour. In another embodiment, the pulse duration is from about 50 milliseconds to about 1 hour. In another embodiment, the pulse duration is from about 100 milliseconds to about 1 hour. In another embodiment, the pulse duration is from about 150 milliseconds to about 1 hour. In another embodiment, the pulse duration is from about 200 milliseconds to about 1 hour. In another embodiment, the pulse duration is from about 250 milliseconds to about 1 hour. In another embodiment, the pulse duration is from about 300 milliseconds to about 1 hour. In another embodiment, the pulse duration is from about 400 milliseconds to about 1 hour. In another embodiment, the pulse duration is from about 500 milliseconds to about 1 hour. In another embodiment, the pulse duration is from about 1 second to about 1 hour.

In one preferred embodiment, the pulse duration is from about 100 milliseconds to about 800 milliseconds. In another preferred embodiment, the pulse duration is from about 100 milliseconds to about 500 milliseconds.

In yet another preferred embodiment, the pulse duration is from about 1 second to about one minute.

In yet another preferred embodiment, the pulse duration is about 250 milliseconds.

In some embodiments, it is more desirable to deliver a continuous wave of light to the targeted area rather than pulsed light, depending on the nature of the targeted area and the actual or anticipated severity of symptoms.

If pulsed light is delivered to the target area, then pulse frequency may be from about 2 to about 10,000 pulses per treatment. In some embodiments, the pulse frequency is from about 10 to about 1,000 pulses per treatment. In other embodiments, the pulse frequency is from about 50 to about 500 pulses per treatment.

In one preferred embodiment, the pulse frequency is from about 75 to about 200 pulses per treatment. In another preferred embodiment, the pulse frequency is about 100 pulses per treatment.

The interval in between pulses is, in one embodiment, from about 0.1 milliseconds to about 1 minute. In another embodiment, the interval in between pulses is from about 0.5 milliseconds to about 30 seconds. In another embodiment, the interval in between pulses is from about 1.0 millisecond to about 10 seconds. In another embodiment, the interval in between pulses is from about 50 milliseconds to about 10 seconds. In a preferred embodiment, the interval in between pulses is from about 75 milliseconds to about 1 second. In a preferred embodiment, the interval in between pulses is between about 100 milliseconds and about 300 milliseconds. In another preferred embodiment, the interval in between pulses is about 100 milliseconds.

The total energy fluence delivered in a single treatment varies based on the specific targeted area or areas being treated and the severity of the symptoms or anticipated symptoms, but will generally be less than about 10 $J/cm^2$ in order to prevent possible side effects. When the light is administered indirectly to the target area, the fluence at the source may be much higher than 10 $J/cm^2$, but the fluence perceived by the source may be very low, due to the absorption and scattering of the light by tissue, bone, or other structures between the light source and the targeted cells. In some cases, a fluence reaching the targeted area may be as low as a few nanojoules.

In a preferred embodiment, the fluence for a single treatment is less than about 1.0 $J/cm^2$. In one preferred embodiment, the fluence for a single treatment is from about 0.1 to about 0.9 $J/cm^2$. In another preferred embodiment, the fluence is about 0.15 $J/cm^2$. In yet another preferred embodiment, the fluence is about 0.10 $J/cm^2$.

In one preferred embodiment, the LED treatment comprises administering light at 590 nm, with a pulse duration of 250 milliseconds, a pulse frequency of 100, with 100 milliseconds in between pulses, at a fluence of 0.15 $J/cm^2$.

It can be advantageous to begin LED treatment prior to the appearance of toxicity to the skin, hair, and nails in order to prevent or treat toxicity associated with VEGF inhibitor treatment. In some embodiments, LED photomodulation treatment begins prior to the administration of VEGF inhibitors. In some embodiments, LED photomodulation treatment begins about 8 weeks, about 7 weeks, about 6 weeks, about 5 weeks, about 4 weeks, about 3 weeks, about 2 weeks, or about 1 week prior to VEGF inhibitor administration. In other embodiments, LED photomodulation treatment begins from about 1 to about 2 weeks prior to VEGF inhibitor administration.

In a preferred embodiment, LED photomodulation treatment begins from about 1 to about 7 days prior to VEGF inhibitor administration. In another preferred embodiment, LED photomodulation treatment begins from about 3 to about 5 days prior to VEGF inhibitor administration.

In other embodiments, LED photomodulation treatment begins following the appearance of toxicity to the skin, hair, and/or nails. In other embodiments, LED photomodulation treatment begins prior to the appearance of toxicity, but following the subject's described discomfort to the skin, hair, and/or nails.

LED photomodulation treatment may be administered daily or at various intervals. Accordingly, LED photomodulation treatment may also be administered every other day, or every two days. In other embodiments, LED photomodulation treatment may be administered once per week, 2 times per week, 3 times per week, 4 times per week or 5 times per week.

In some embodiments, on days on which LED photomodulation treatment is administered, LED photomodulation treatment is administered once per day, twice per day, 3 times per day, or 4 times per day. In other embodiments LED photomodulation treatment is administered more than 4 times per day, depending on the desired effect of the treatment and the severity of the toxicity to be treated.

In some embodiments, when at least some of the LED photomodulation treatment is administered to a subject on the same day as the administration of VEGF inhibitor, the LED photomodulation treatment is administered prior to the administration of VEGF inhibitor. In other embodiments, when at least some of the LED photomodulation treatment is administered on the same day as the administration of VEGF inhibitor, the LED photomodulation treatment is administered following the administration of VEGF inhibitor.

In some embodiments, the total duration of LED photomodulation treatment a subject receives in a day is about 1 hour or less, and in other embodiments is about 30 minutes or less. In other embodiments, the total duration of LED photomodulation a subject receives in a day is about 25 minutes or less, about 20 minutes or less, about 15 minutes or less, or about 10 minutes or less. In a preferred embodiment, the total duration of LED photomodulation treatment a subject receives in a day is about 5 minutes or less. In another preferred embodiment, the total duration of LED photomodulation treatment a subject receives in a day is about 1 minute or less. In another preferred embodiment, the total duration of LED photomodulation treatment a subject receives in a day is about 30 seconds or less.

In some embodiments, LED photomodulation treatment is administered to a subject until the final dose of VEGF inhibitor is administered. In other embodiments, LED photomodulation treatment continues following the final dose of VEGF inhibitor, or for as long as it continues to exert a beneficial effect on the area or areas being treated. In some embodiments, LED photomodulation treatment continues from about one week to about 16 weeks following the final dose of VEGF inhibitor. In some embodiments, LED photomodulation treatment continues from about one week to about 12 weeks or more, following the final dose of VEGF inhibitor. In some embodiments, LED photomodulation treatment continues from about one week to about 8 weeks following the final dose of VEGF inhibitor. In other embodiments, LED photomodulation treatment continues from about one week to about 4 weeks following the final dose of VEGF inhibitor.

In some embodiments, LED photomodulation treatment is initiated following the final dose of VEGF inhibitor. Depending on the duration of LED photomodulation treatment, the frequency with which LED photomodulation treatment is administered may change over time. In some embodiments, LED photomodulation treatment continues from about one week to about 8 weeks following the final dose of VEGF inhibitor. In other embodiments, LED photomodulation treatment continues from about one week to about 8 weeks following the final dose of VEGF inhibitor. In a preferred embodiment, LED photomodulation treatment continues for about 4 weeks following the final dose of VEGF inhibitor. In another preferred embodiment, LED photomodulation treatment continues for about 30 days following the final dose of VEGF inhibitor. In another preferred embodiment, LED photomodulation treatment continues from about 10 days to about 90 days following the final dose of VEGF inhibitor. In another preferred embodiment, LED photomodulation treatment continues from about 10 days to about 60 days following the final dose of VEGF inhibitor.

In some embodiments, LED photomodulation treatment is continued until the toxicity to be treated or its symptoms have improved, or until symptoms are no longer present or until the toxicity has been eliminated. In some embodiments, the toxicity or symptoms to be ameliorated, prevented, or treated include but are not limited to one or more of a subject's discomfort, pain, itching, sensitivity to touch, swelling, discoloration, burning, or change in hair amount, texture, or pattern on the head, eyelashes, eyebrows, or elsewhere on the body.

In some embodiments, the LED photomodulation treatment is administered in order to prevent or treat one or more of a subject's discomfort, pain, itching, sensitivity to touch, swelling, discoloration, or burning associated with the administration of one or more VEGF inhibitors.

In some embodiments, LED photomodulation treatment begins following the final dose of VEGF inhibitor, and continues from about one day to about 8 weeks, or longer. In other embodiments, LED photomodulation treatment begins following the final dose of VEGF inhibitor, and continues until symptoms have improved or until symptoms are no longer present, or while the LED photomodulation treatment continues to have a beneficial effect on the area or areas treated.

The method of the invention comprising LED photomodulation treatment for the prevention or treatment of toxicity to the skin, hair and/or nails may be used in combination with other treatments or agents for toxicities to the skin, hair and/or nails. These additional treatments or agents may aid in treating the toxicity or may alleviate or eliminate the symptoms associated with the toxicity. The additional treatments or agents may also aid in the effectiveness of the LED therapy. In some embodiments, LED photomodulation treatment is used in combination with one or more agents, which include but are not limited to skin moisturizers; lotions; sunscreens; topical anti-inflammatory agents; topical steroids; oral steroids; topical antibiotics; oral antibiotics; topical cleansers; white vinegar soaks; aluminum soaks; Burrow's solution; Monsel's solution; silver nitrate; thymol, emollients such as Bag Balm and Petroleum jelly; mild soap; solutions of ammonium lactate, salicylic acid and urea; protective coverings; zinc oxide cream; liquid cyanoacrylate preparations; warm compresses; analgesics; tacrolimus cream; artificial tears; and antifungal agents.

Oral or topical antibiotics may, for example, include tetracylcine, minocycline, doxycyline, polymyxin B, Clindamycin, and Neomycin.

Topical steroids may include, for example, hydrocortisone cream and dexamethasone ointment.

Sunscreen may include, for example, that which is PABA free, preferably with UVA/UVB protection. In some embodiments, the sunscreen has an SPF of ≥15. Use of sunscreens with higher SPF values may require use of LED treatments that deliver higher energy fluence.

In one preferred embodiment, the agents administered in combination with LED photomodulation treatment, whether administered prior to LED treatment, simultaneously with LED treatment, extending, optionally beyond LED treatment, or which are administered following LED treatment, are lotion products containing copper.

The VEGF inhibitors contemplated for use according to the methods of the present invention can be any drug which acts as an inhibitor of the VEGF or one or more of its receptors. Such inhibitors include those already known to those of skill in the art, but may include inhibitors subsequently developed. The VEGF inhibitors may be antibodies targeting VEGF or one or more of its receptors, they may be small molecules, or they may be any other class of agents. VEGF inhibitors include, but are not limited to any tyrosine kinase inhibitors, bevacizumab, ranibizumab, sunitinib, sorafenib, axitinib, pazopanib, vatalanib, pazopanib, sutinib, telatinib, semaxanib, VEGF Trap, HuMV833, IMC-1121B, VEGFR-TK1, AEE 788, AMG-706, AZD 2171, AZD 6474, BIBF 1120, BMS 582664, CHIR 258, CP-547,632, KRN 951, SU 6668, SU 14813, XL 647, XL 999, and ZK 304709.

Toxicity as used herein refers to any untoward reactions to the administration of any one or more VEGF inhibitors.

This invention encompasses preventing and treating toxicity of the external surface of the body, including the skin, hair, and/or nails, wherein the toxicity is associated with the administration of one or more VEGF inhibitors. The invention also encompasses preventing and treating toxicity to any part of the skin which is not on the external surface of the body, such as the dermal and subcutaneous layers of the skin, and any structure or portion found within any of these layers, and any structure or portion that may traverse any of these layers, including, but not limited to hair follicles and sebaceous glands. The treatment according to the invention comprises using LED photomodulation treatment in patients for which one or more VEGF inhibitors might be indicated, such patients with cancer, for example. In addition, the invention embodies preventing or treating toxicity of the skin, hair, and/or nails associated with the administration of one or more VEGF inhibitors with LED photomodulation treatment in patients administered one or more VEGF inhibitors for any indication other than cancer for which one or more VEGF inhibitors might be indicated.

The method of the invention contemplates treating both short-term and long-term toxicities of the skin, hair, and nails associated with the administration of one or more VEGF inhibitors. Short-term toxicities comprise those which improve within about 3 months following the discontinuation of treatment with VEGF inhibitors. Long-term toxicities comprise those which do not improve within about 3 months following the discontinuation of treatment with VEGF inhibitors. Most short-term toxicities resolve within about 1 to about 3 months.

In one embodiment, LED photomodulation is administered to patients to prevent or treat conditions of the skin associated with VEGF inhibitors, and in particular to prevent or treat rashes of the skin associated with VEGF inhibitors. While acne is a rash caused by propionibacteria, the acneiform rashes associated with VEGF inhibitors, that are prevented or treated by the method of the invention are not a result of bacteria. In one embodiment, the invention prevents or treats rashes that comprise acneiform rashes that are not associated with bacteria.

The method of the invention encompasses preventing or treating, in some preferred embodiments, a papulopustular rash associated with the administration of one or more VEGF inhibitors. In another embodiment, the method of the invention prevents or treats a maculo-papular rash associated with the administration of one or more VEGF inhibitors. In another embodiment of the invention, dermatitis associated with the administration of one or more VEGF inhibitors may be prevented or treated. In yet another embodiment, the invention encompasses preventing or treating a morbilliform rash associated with the administration of one or more VEGF inhibitors.

In one preferred embodiment, the method of the invention prevents or treats skin toxicity associated with VEGF inhibitor treatment in the form of palmar-plantar erythrodysesthesia (also referred to as "hand-foot syndrome"), or at least one of the symptoms of hand-foot syndrome. For example, the method of the invention prevents or treats erythematous swellings over the fingertips and periungual area, blisters with erythematous halos over the palms of the hands and soles of the feet, as well as acanthosis and fungiform pustules.

The method of the invention also prevents or treats toxicity of the skin, hair, and nails following the discontinuation of treatment with VEGF inhibitors.

In certain embodiments, the method of the invention encompasses preventing or treating one or more of the following, which are associated with the administration of one or more VEGF inhibitors: psoriasis, hypopigmentation, hyperpigmentation, fissures, pruritis, xerosis, and telangiectasias.

The method of the invention also comprises preventing or treating toxicities to the nails that are associated with the administration of VEGF inhibitors. In certain embodiments, the method of the invention encompasses preventing or treating paronychia associated with the administration of one or more VEGF inhibitors. The method of the invention further contemplates preventing or treating secondary infections of the nail beds that are associated with the administration of one or more VEGF inhibitors.

The methods of the invention also comprise preventing or treating toxicities of the eyelids that are associated with the administration of VEGF inhibitors, including, but not limited to blepharitis, ectropion and entropion.

The method of the invention further comprises treating or preventing disturbances to the normal hair growth cycle that are associated with administration of VEGF inhibitors. In one embodiment, the method of the invention encompasses preventing or treating hair loss or alopecia associated with the administration of one or more VEGF inhibitors. In yet other embodiments, the invention encompasses preventing or treating increases in the amount of and/or texture of facial hair associated with administration of one or more VEGF inhibitors, and preferably, in women. In yet other embodiments, the method of the invention encompasses preventing or treating changes in the texture or amount of hair on the head or on the eyebrows, that are associated with the administration of one or more VEGF inhibitors.

Administration of VEGF inhibitors is also associated with alterations in the texture, length, and direction of growth of eyelashes. In one embodiment, the method of the invention encompasses preventing or treating trichomegaly and/or hypertrichosis associated with the administration of one or more VEGF inhibitors.

The National Cancer Institute (NCI) classifies rashes according to the NCI Common Toxicity Criteria (NCI-CTC), and includes categories that range from grade 1 to grade 4.

Grade 1 comprises macular or papular eruption or erythema with or without associated symptoms. Grade 2 comprises macular or papular eruption, or erythema with pruritus or associated symptoms covering less than 50% of the body surface or localized desquamation or other lesions covering less than 50% of the body surface. Grade 3 comprises symptomatic, generalized erythroderma, maculopapular, vesicular eruption or desquamation covering greater than or equal to 50% of the body surface. Grade 4 comprises generalized exfoliative dermatitis, ulcerative dermatitis, or bullous dermatitis.

This invention contemplates preventing or treating any of NCI-CTC grade 1 to grade 4 rashes, including any rashes that might be in between stages or that can be described by more than one stage or by other means of classification.

In some embodiments, the method of the invention is used to prevent or treat NCI-CTC-grade 1 rashes, grade 2 rashes, grade 3 rashes, or grade 4 rashes associated with VEGF inhibitor treatment.

The method of the invention also encompasses treating any areas of skin that are affected by the administration of one or more VEGF inhibitors. In some embodiments, the method of the invention is used to prevent or treat toxicity to the skin present on one or more of the face, forehead, chest, back, neck, arms, legs, shoulders, hands, feet, fingers, toes, palms of hands, soles of feet, or the scalp, or any other area of skin on a human which may be affected by treatment with VEGF inhibitors. The method of the invention also encompasses treating any areas of toenails or fingernails that are affected by the administration of one or more VEGF inhibitors, as well as growth of toenails or fingernails.

In a preferred embodiment, the method of the invention is used to prevent or treat skin toxicities on the face or forehead associated with VEGF inhibitor treatment. In another preferred embodiment, the method of the invention is used to prevent or treat skin toxicities on the chest or back. In yet another preferred embodiment, the invention is used to prevent or treat toxicities on the hands or feet.

In other embodiments, the invention encompasses preventing or treating blisters and erythema of the hands and feet, which are often under pressure due to walking and other activity, and which VEGF inhibitors make susceptible to such injury due to damage that VEGF inhibitors cause to the capillary endothelia.

Infectious complications of the skin, hair, or nails may occur from VEGF inhibitor administration. The invention also encompass preventing or treating any kind of infections in any areas of skin, hair, or nails that are affected by the administration of one or more VEGF inhibitors. These infections may be, but are not limited to, bacterial infections such as Impetigo or Dissecting cellulitis, viral infections, and fungal infections.

The method of the invention encompasses preventing or treating inflammation of any areas of skin, hair, or nails that is associated with the administration of one or more VEGF inhibitors.

In a preferred embodiment, the method of the invention prevents or treats an inflammatory rash on any one or more areas of the skin, associated with administration of one or more VEGF inhibitors.

In one embodiment, a method is provided for reducing vascular dilatation in the skin, that is associated with the administration of VEGF inhibitors.

In another embodiment, a method is provided for reducing permeability and reducing activation of nociceptive fibers in skin, skin, that is associated with the administration of VEGF inhibitors.

In another embodiment, the invention provides for improved wound healing on the skin of a subject, by using LED photomodulation therapy.

The method of the invention also comprises preventing or treating toxicities of the skin, hair, or nails that are associated with the administration of VEGF inhibitors and one or more additional agents that are administered to a subject as part of cancer treatment, or as part of the treatment for any other disorder for which EGRF inhibitors are indicated, either concurrently or within one or a plurality of days of administration of an VEGF inhibitor. The additional agent(s) administered to a subject as part of cancer treatment or other treatment might exacerbate the toxicity associated with the one or more VEGF inhibitors.

EXAMPLES

It is understood that the following examples and embodiments described herein are for illustrative purposes only and that various modifications or changes in light thereof will be suggestive to persons skilled in the art and are to be included within the spirit and purview of this application and the scope of the appended claims. All publications, patents, and patent applications cited herein are hereby incorporated by reference in their entirety for all purposes.

Example 1

LED Treatment Improves Dermatologic Toxicities Associated with VEGF Inhibitors

Ten cancer patients are assessed who have been administered and continue to receive VEGF inhibitor therapy. The patients each have rashes manifesting either as hand-foot syndrome, a papulopustular rash that is present mostly on the face and hands, or other toxicities to the skin, hair, and/or nails and which are associated with VEGF inhibitor therapy. The rashes on each patient are classified between 2 and 4 on the NCI-CTC scale.

LED photomodulation treatment is administered to the patients following the appearance of the rashes. The Gentle Waves® LED device (LightBioScience, LLC, Virginia Beach, Va.) is used to administer the light. LED treatments are administered at a preset cycle, 590 nm, standard 100-pulse, 250 milliseconds per pulse at a fluence of 0.15 J/cm$^2$. LED phototherapy is administered to each patient daily for four weeks.

It is contemplated that all of the patients respond well and quickly to the treatment. It is contemplated that after the first three treatments, the rashes are noticeably reduced and the associated pain is improved. It is also contemplated that the rashes continue to improve over the course of treatment.

Example 2

LED Treatment Improves Hand-Foot Syndrome Associated with VEGF Inhibitors

One patient was assessed who had been administered VEGF inhibitor therapy. The patient exhibited hand-foot syndrome, which included erythematous swellings over the fingertips and periungual area, and blisters with erythematous halos over the palms of the hands and soles of the feet. These dermatological symptoms were associated with the patient's VEGF inhibitor therapy.

LED photomodulation treatment was administered to the patient following the appearance of the severe rash. The Gentle Waves® LED device (LightBioScience, LLC, Virginia Beach, Va.) was used to administer the light. LED treatments were administered at a preset cycle, 590 nm, standard 100-pulse, 250 milliseconds per pulse at a fluence of 0.15 J/cm$^2$. LED phototherapy was administered to the patient daily for two weeks.

The patient responded well and quickly to the treatment. After the first three treatments, the patient noted improvement in how the skin felt. After the first week of treatment, visible signs of healing were noted, in that the rash appeared less severe.

Certain modifications and improvements will occur to those skilled in the art upon a reading of the foregoing description. It should be understood that all such modifications and improvements have been deleted herein for the sake of conciseness and readability but are properly within the scope of the following claims.

The invention claimed is:

1. A method of treating or preventing skin toxicity associated with administration of a vascular endothelial growth factor (VEGF) inhibitor in a subject in need thereof, said method, comprising
    directing light onto a target area on said subject, wherein said subject is administered a VEGF inhibitor therapy, said light being emitted from one or more light emitting diode (LED) sources producing at least one range of wavelengths of light,
    said light comprising about 90% of a wavelength of about 590 nm and about 10% of a wavelength of about 870 nm,
    said light further comprising pulses of light that are 250 ms in duration that are separated by 100 ms, and are repeated 100 times,
    wherein skin toxicity is in the dermis and is treated or prevented in the subject.

2. The method according to claim 1, wherein said toxicity is associated with inflammation of said skin.

3. The method according to claim 1, wherein said VEGF inhibitor is selected from the group consisting of bevacizumab, sunitinib and sorafenib.

4. The method according to claim 1, wherein said skin toxicity is in the epidermis.

5. The method according to claim 1, wherein said skin toxicity is in the subcutaneous layer of the skin.

6. The method according to claim 1, wherein said skin toxicity is an acneiform rash that is not caused by bacteria.

7. The method according to claim 1, wherein said skin toxicity is a papulopustular rash.

8. The method according to claim 1, wherein said skin toxicity is pruritis.

9. The method according to claim 1, wherein said skin toxicity comprises palmar-plantar erythrodysesthesia.

10. The method according to claim 1, wherein said skin toxicity comprises one or more symptoms of palmar-plantar erythrodysesthesia.

11. The method according to claim 1, wherein said skin toxicity is classified as an NCI-CTC grade 1, grade 2, grade 3, or grade 4 rash.

12. The method according to claim 11, wherein said skin toxicity is classified as an NCI-CTC grade 2.

13. The method according to claim 1, further comprising administration of one or more additional agents.

14. The method according to claim 13, wherein the agent is lotion containing copper.

15. The method according to claim 1, wherein the target area is selected from the group consisting of the face, neck, back, scalp, hands, and feet.

16. The method according to claim 1, wherein the LED source emits light at a wavelength from 500 nm to 700 nm.

17. The method according to claim 1, wherein the LED source emits light at a wavelength of 590 nm.

18. The method according to claim 1, wherein the light from the LED source is administered once daily.

19. The method according to claim 1, wherein the light from the LED source is administered beginning prior to the administration of VEGF inhibitor therapy.

20. The method according to claim 1, wherein the light from the LED source is administered concurrent with the administration of VEGF inhibitor therapy.

21. The method according to claim 1, wherein the light from the LED source is administered following an initial dose of VEGF inhibitor therapy.

22. The method according to claim 1, wherein the LED delivers a total energy fluence of $0.15$ J/cm$^2$.

* * * * *